(12) United States Patent
Georgeson et al.

(10) Patent No.: US 7,484,413 B2
(45) Date of Patent: Feb. 3, 2009

(54) REMOTE RADIUS INSPECTION TOOL FOR COMPOSITE JOINTS

(75) Inventors: Gary E. Georgeson, Federal Way, WA (US); Michael D. Fogarty, Auburn, WA (US)

(73) Assignee: The Boeing Company, Chicago, IL (US)

( * ) Notice: Subject to any disclaimer, the term of this patent is extended or adjusted under 35 U.S.C. 154(b) by 436 days.

(21) Appl. No.: 11/261,222

(22) Filed: Oct. 28, 2005

(65) Prior Publication Data

US 2006/0042391 A1 Mar. 2, 2006

Related U.S. Application Data

(63) Continuation-in-part of application No. 10/752,890, filed on Jan. 7, 2004, now Pat. No. 7,231,826, and a continuation-in-part of application No. 10/734,452, filed on Dec. 12, 2003, now Pat. No. 6,993,971.

(51) Int. Cl.
*G01N 29/265* (2006.01)
(52) U.S. Cl. .............................. 73/624; 73/633; 73/634; 73/866.5
(58) Field of Classification Search .................. 73/618, 73/620, 623, 624, 633, 636, 866.5
See application file for complete search history.

(56) References Cited

U.S. PATENT DOCUMENTS

| | | | |
|---|---|---|---|
| 2,005,035 A | 6/1935 | Houtman | |
| 2,459,162 A | 1/1949 | Hayes | |
| 3,121,324 A | 2/1964 | Cowan | |
| 3,791,201 A | 2/1974 | Dory | |
| 4,010,636 A | 3/1977 | Clark et al. | |
| 4,018,082 A * | 4/1977 | Manoliu et al. | 73/600 |
| 4,117,733 A | 10/1978 | Gugel | |
| 4,185,501 A | 1/1980 | Proudian et al. | |
| 4,200,885 A | 4/1980 | Hofstein | |
| 4,361,044 A | 11/1982 | Kupperman et al. | |
| 4,399,703 A | 8/1983 | Matzuk | |
| 4,466,286 A | 8/1984 | Berbeé et al. | |
| 4,526,037 A | 7/1985 | Wentzell et al. | |

(Continued)

FOREIGN PATENT DOCUMENTS

EP 1 214 909 6/2002

OTHER PUBLICATIONS

International Search Report for PCT/US2006/041373 dated Jun. 14, 2007.

*Primary Examiner*—Hezron Williams
*Assistant Examiner*—Rose M Miller
(74) *Attorney, Agent, or Firm*—Alston & Bird LLP (57) ABSTRACT

There is provided a non-destructive inspection device having an actuating portion and at least one inspecting portion. The inspecting portion(s) are magnetically coupled to the actuating portion so that the inspecting portion(s) may be moved into limited-access areas to inspect features of a structure. The inspecting portion(s) each include at least one inspection sensor that transmits and/or receives signals that, when processed, indicate defects in the features of the structure. The inspection sensor of the inspecting portion is moveable relative to the housing of the inspecting portion to enable inspection of relatively larger areas of the structure being inspected. The inspection sensors may be moved, relative to the housing of the inspecting portion, manually and/or automatically.

21 Claims, 10 Drawing Sheets

U.S. PATENT DOCUMENTS

| | | | |
|---|---|---|---|
| 4,541,434 A | 9/1985 | Okado | |
| 4,612,808 A | 9/1986 | McKirdy et al. | |
| 4,807,476 A | 2/1989 | Cook et al. | |
| 4,848,159 A | 7/1989 | Kennedy et al. | |
| 4,862,748 A | 9/1989 | Woodmansee | |
| 4,980,872 A | 12/1990 | Oler et al. | |
| 5,031,458 A * | 7/1991 | Young et al. | 73/636 |
| 5,062,301 A | 11/1991 | Aleshin et al. | |
| 5,203,869 A | 4/1993 | Bashyam | |
| 5,343,750 A | 9/1994 | Bashyam | |
| 6,131,460 A * | 10/2000 | Brunty et al. | 73/634 |
| 6,180,928 B1 | 1/2001 | Garrigus | |
| 6,722,202 B1 | 4/2004 | Kennedy et al. | |
| 6,848,312 B2 * | 2/2005 | Georgeson | 73/627 |
| 7,228,741 B2 * | 6/2007 | Georgeson et al. | 73/634 |
| 7,231,826 B2 * | 6/2007 | Bossi et al. | 73/618 |
| 7,240,556 B2 * | 7/2007 | Georgeson et al. | 73/641 |
| 7,249,512 B2 * | 7/2007 | Kennedy et al. | 73/618 |
| 7,263,889 B2 * | 9/2007 | Kennedy et al. | 73/620 |
| 7,313,959 B2 * | 1/2008 | Georgeson et al. | 73/620 |
| 7,315,609 B2 * | 1/2008 | Safai et al. | 378/57 |
| 7,320,249 B2 * | 1/2008 | Georgeson et al. | 73/634 |
| 2002/0006079 A1 | 1/2002 | Saito et al. | |
| 2002/0017140 A1 | 2/2002 | Georgeson et al. | |
| 2003/0221306 A1 | 12/2003 | Day et al. | |
| 2005/0126294 A1 * | 6/2005 | Bossi et al. | 73/629 |
| 2005/0145033 A1 * | 7/2005 | Bossi et al. | 73/620 |
| 2006/0010980 A9 * | 1/2006 | Bossi et al. | 73/620 |
| 2006/0053891 A1 * | 3/2006 | Georgeson et al. | 73/624 |
| 2006/0055399 A1 * | 3/2006 | Georgeson et al. | 324/232 |

* cited by examiner

REMOTE RADIUS INSPECTION TOOL FOR COMPOSITE JOINTS

CROSS-REFERENCES TO RELATED APPLICATIONS

This application is a continuation-in-part of U.S. patent application Ser. No. 10/734,452, filed on Dec. 12, 2003, now U.S. Pat. No. 6,993,971 and U.S. patent application Ser. No. 10/752,890, filed on Jan. 07, 2004, now U.S. Pat. No. 7,321,971 which are hereby incorporated herein in their entirety by reference.

FIELD OF THE INVENTION

The present invention relates generally to non-destructive inspection devices. More particularly the invention relates to an inspection device for inspecting limited-access features of a structure.

BACKGROUND OF THE INVENTION

Non-destructive inspection of structures involves thoroughly examining a structure without harming the structure or requiring significant disassembly of the structure. Non-destructive inspection is advantageous for many applications in which a thorough inspection of the exterior and/or interior of a structure is required. For example, non-destructive inspection is commonly utilized in the aircraft industry to inspect aircraft structures for any type of internal or external damage to the structure.

Among the structures that are routinely non-destructively inspected are composite structures. In this regard, composite structures are commonly used throughout industry because of their engineering qualities, design flexibility, and low weight. As such, it is frequently desirable to inspect composite structures to identify any flaws, such as cracks, voids, or porosity, which could adversely affect the performance of the composite structure.

Various types of sensors may be utilized to perform non-destructive inspection. One or more sensors may move over the structure to be examined and receive data regarding the structure from which internal flaws can be identified. For example, a pulse-echo, thru-transmission, or shear wave sensor may be utilized to obtain ultrasonic data, such as thickness gauging, detection of laminar defects and porosity, and/or crack detection in the structure. Resonance, pulse echo, or mechanical impedance sensors may also be utilized to provide indications of voids or porosity, such as in adhesive bondlines of the structure. The data acquired by the sensors is typically processed by a processing element, and the processed data may be presented to a user via a display.

Accessibility to the features of the structure requiring inspection is one consideration in choosing a non-destructive inspection device. Access to the feature requiring inspection may be so limited that a manual inspection by a technician is not possible. An example of a structure with limited access is an internal joint of a wing structure. More specifically, the bondlines produced by close-out joints created when the last sections of the wing are attached exemplify the limited-access features of a structure.

Limited-access features of a structure, such as the close-out joints, are difficult to fully inspect using contemporary joints inspection devices. Accordingly, a need exists for a convenient and reliable non-destructive inspection device to inspect limited-access features of a structure.

BRIEF SUMMARY OF THE INVENTION

Embodiments of the present invention address the needs and achieve other advantages by providing a non-destructive inspection device for inspecting a feature of a structure, such as a limited-access feature. The inspection device includes an actuating portion and at least one inspecting portion that are magnetically coupled so that the inspecting portion moves in concert with the actuating portion. The inspecting portion includes a housing, an inspection sensor, and at least one magnet. The actuating portion also includes at least one magnet so that when the actuating portion is placed on a first surface of the structure and the inspecting portion is positioned on a surface of the structure opposite the first surface, the two portions are magnetically coupled so that movement of the actuating portion causes the inspecting portion to move in concert with the actuating portion without the inspecting portion directly contacting the actuating portion. In addition, the inspection sensor is selectively moveable relative to the housing of the inspecting portion. Thus, the inspecting portion can be moved to be proximate the feature of the structure to inspect the feature and the inspection sensor can be moved to inspect various portion of the feature.

Additional embodiments of the present invention include a second inspecting portion that further includes a second inspection sensor that is selectively moveable relative to a housing of the second inspecting portion. Further embodiments of the present invention include inspection sensors that comprise ultrasonic transducers, ultrasonic wheel transducers, airborne ultrasonic transducers, or laser ultrasonic transducers, to list non-limiting examples. The inspection sensor is selectively moveable in a direction that is generally toward and/or away from the actuating portion and/or that is generally aligned with the direction of motion of the actuating portion(s) and inspecting portion(s).

A method of inspecting a structure is also provided by the present invention. To inspect the structure, an actuating portion of a non-destructive inspection device is placed on a first surface of the structure and at least one inspecting portion of the non-destructive inspection device is positioned on a surface of the structure opposite the first surface. At least one magnet in the inspecting portion magnetically couples to at least one magnet in the actuating portion. The actuating portion is moved on the surface of the structure such that the inspecting portion is moved in concert with the actuating portion. In addition, the inspection device of the inspecting portion is moved relative to the housing of the inspecting portion. The inspection sensor creates an output that can be monitored by the technician to find flaws or defects. Accordingly, the non-destructive inspection device and inspection method provide for convenient and reliable inspection of features of a structure.

BRIEF DESCRIPTION OF THE SEVERAL VIEWS OF THE DRAWINGS

Having thus described embodiments of the invention in general terms, reference will now be made to the accompanying drawings, which are not necessarily drawn to scale, and wherein:

DETAILED DESCRIPTION OF THE INVENTION

At least six embodiments of the present invention will be described more fully with reference to the accompanying drawings. The invention may be embodied in many different forms and should not be construed as limited to only the embodiments described and shown. Like numbers refer to like elements throughout.

With reference to FIGS. 1-13, non-destructive inspection devices in accordance with various embodiment of the present invention are illustrated. Referring to the embodiment of FIGS. 1-3, the non-destructive inspection device 10 includes an actuating portion 12, a first inspecting portion 14, and a second inspecting portion 16. The actuating portion 12 and the inspecting portions 14 and 16 are individual portions and are not directly connected in the illustrated embodiment. The actuating portion 12 is structured for placement on a surface of the structure undergoing inspection. The inspecting portions 14 and 16 are structured for positioning on a surface opposite the surface the actuating portion is placed.

The actuating portion 12 includes at least one first magnet 20 and at least one second magnet 22 for magnetically coupling with at least one magnet 24 of the first inspecting portion 14 and with the at least one magnet 26 of the second inspecting portion 16. The magnetic coupling provides a remote connection between the actuating portion 12 and the inspecting portions 14 and 16 so that the inspecting portions move in concert with the actuating portion. The inspecting portions 14 and 16 move in concert with the actuating portion 12 such that the inspecting portions maintain substantially consistent positions relative to the actuating portion while the inspecting portions are magnetically coupled to the actuating portion. The actuating portion 12 of FIG. 1 also includes a handle 18 that connects the at least one first magnet 20 to the at least one second magnet 22. The at least one first magnet 20 magnetically couples with the magnet 24 of the first inspecting portion 14 during operation of the inspection device 10. Likewise, the at least one second magnet 22 of the actuating portion 12 magnetically couples with the magnet 26 of the second inspecting portion 16 during operation of the inspection device 10. The at least one first magnet 20 is magnetically coupled to the magnet 24 of the first inspecting portion 14 when the actuating portion 12 and the first inspecting portion are positioned on opposite surfaces of a structure 30, as shown in FIGS. 2 and 3. The magnets are advantageously positioned such that the magnets are proximate the opposed surfaces 32 and 34 of the structure 30 such that the magnetic coupling therebetween is maximized. Similarly, the at least one second magnet 22 is magnetically coupled to the magnet 26 of the second inspecting portion 16 when the actuating portion 12 and the second inspecting portion are positioned on opposite surfaces of the structure 30. The magnets are advantageously positioned such that the magnets are proximate the opposed surfaces 32 and 36 of the structure 30 such that the magnetic coupling therebetween is maximized.

The magnets 20, 22, 24, and 26 of the illustrated embodiment, shown in FIGS. 1-13 are preferably pancake magnets formed of neodymium iron boron, which advantageously have greater magnetic flux (around 12,000 gauss) than standard ceramic or ferrite magnets (around 3,900 gauss). Further embodiments of the invention include magnets of different material, such as Samarium Cobalt or Alnico to list two non-limiting examples of alternative magnets, and/or may create the magnetic coupling with electromagnets or other magnetic coupling means. The present invention may further comprise magnetic shunting mechanisms to control the magnetic flux of the magnetic couplings, a non-limiting example being rare earth metal switched magnetic devices disclosed in U.S. Pat. No. 6,180,928 that is assigned to the present assignee. Still further embodiments of the present invention include a plurality of magnets, such as four magnets to list one non-limiting example, to provide the magnetic coupling between the actuating portion and an inspecting portion.

Structures 30 that may be inspected with the inspection device 10 of the present invention may include but are not limited to composites, non-ferromagnetic metals (e.g. aluminum alloy, titanium alloy, or aluminum or titanium hybrid laminates such as GLARE or Ti/Gr), and polymers. It should be noted that the first surface 32, the surfaces 34 and 36 as illustrated in FIG. 2, and the material therebetween, which collectively define the material through which the actuating portion 12 and the inspecting portions 14 and 16 are magnetically coupled, preferably comprise a non-ferromagnetic material because the magnetic coupling would be diminished or eliminated by a ferromagnetic material located between the actuating portion and the inspecting portions.

The magnets 24 and 26 support the inspecting portions 14 and 16, respectively, and keep each of the inspecting portions substantially aligned. Each magnet 20, 22, 24, and 26 comprises at least one individual magnet. However, further embodiments of the present invention that comprise a plurality of magnets preferably arrange the magnets in patterns that are substantially aligned with and magnetically coupled to the corresponding plurality of magnets to thereby provide maximum coupling of the magnets.

Referring to FIGS. 2 and 3, the structure 30 includes a feature 40 that extends outwardly from the surfaces 34 and 36 of the structure, such as perpendicular thereto. As shown in FIG. 2, the feature 40 of a structure 30 may be a limited-access feature such as a shear tie or spar that is bonded or fastened to the skin or joined to or protruding from the surfaces 34 and 36. The feature 40 may also include a pi joint 42 connecting the feature to the surfaces 34 and 36, wherein the actual joint may be inspected by the inspection device 10. Alternative features to be inspected may be a feature of any shape, angular orientation, size, or location. The feature 40 of FIGS. 2 and 3 represents an interior rib of a wing structure comprising a composite material for use in the aerospace industry; however, the feature 40 may represent any portion of any structure to be non-destructively inspected. Furthermore, the feature 40 may be of any material that may be non-destructively inspected, including ferromagnetic material. If no magnetic coupling is required through the feature 40 to be inspected, a structure 30 having a feature comprising a ferromagnetic material may be inspected if the material through which the actuating portion 12 and inspecting portions 14 and 16 are magnetically coupled comprises a non-ferromagnetic material. Such a structure 30 would typically be used for non-aerospace applications because of the importance of minimal weight in aerospace applications and a ferromagnetic feature 40 would usually be heavier than a non-ferromagnetic feature such as a composite feature. The inspection sensors used to inspect a ferromagnetic feature 40 preferably are impervious to the magnetic fields created by the magnetic couplings between the actuating portion and inspecting portions.

The feature 40 of the illustrated embodiment includes a first face 44 facing the first surface 34 and a second face 46 facing the second surface 36. When the inspection device 10 is positioned on the structure 30, as shown in FIGS. 2 and 3, the feature 40 is located between the first inspecting portion 14 and the second inspecting portion 16. Further embodiments of the inspection device may include only one inspecting portion with at least one inspection sensor for non-destructive inspection of the feature 40, i.e., one-sided inspection relying on the reflection of signals from within the feature or viewing the feature with an optical borescope or miniature camera. One-sided ultrasonic inspection methods such as pitch catch, pulse echo, resonance, mechanic impedance, etc. are non-limiting examples of one-sided inspection techniques of further embodiments of the present invention comprising one or more inspecting portions.

Figure 1:
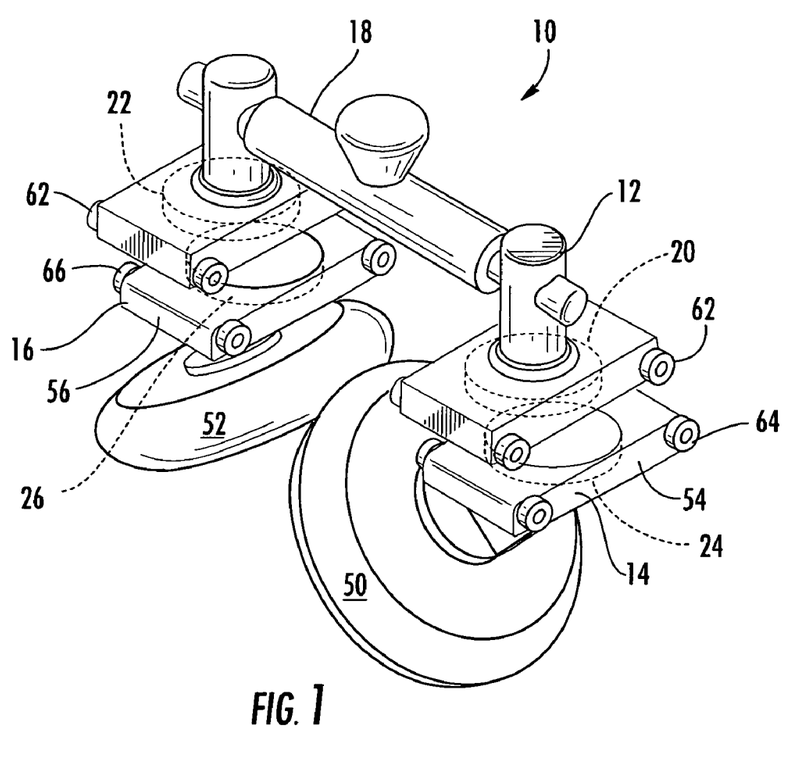
FIG. 1 is a perspective view of a non-destructive inspection device in accordance with one embodiment of the present invention, illustrating an actuating portion and two inspecting portions wherein the inspection sensors are moveable relative to the housing of the respective inspecting portion and the inspection sensors define ultrasonic wheel transducers.
Figure 2:
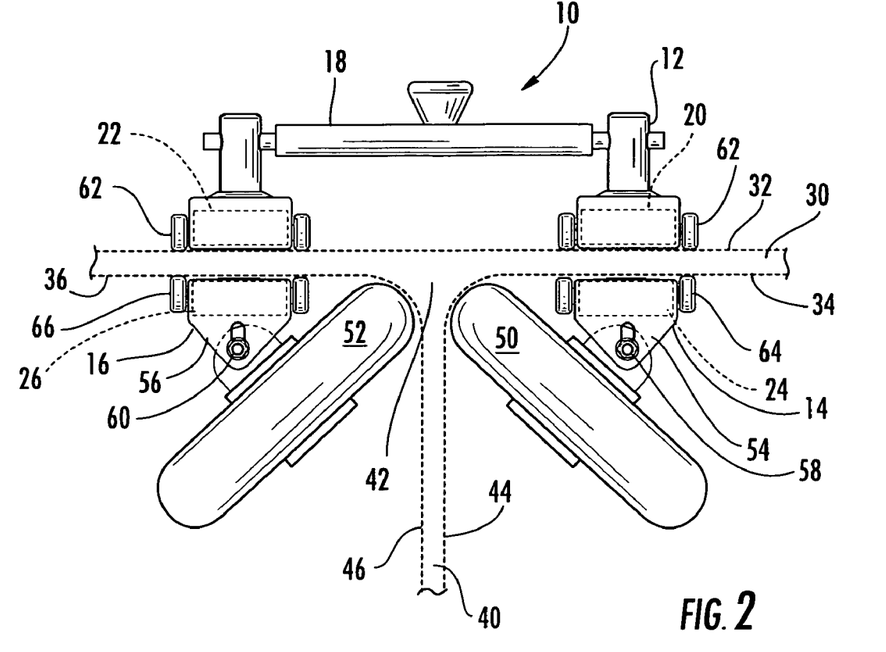
FIG. 2 is a side planar view of the inspection device of FIG. 1, illustrating the inspection device positioned on a structure to inspect limited access features of the structure, wherein the inspection sensors are in a first position relative to the respective housing.
Figure 3:
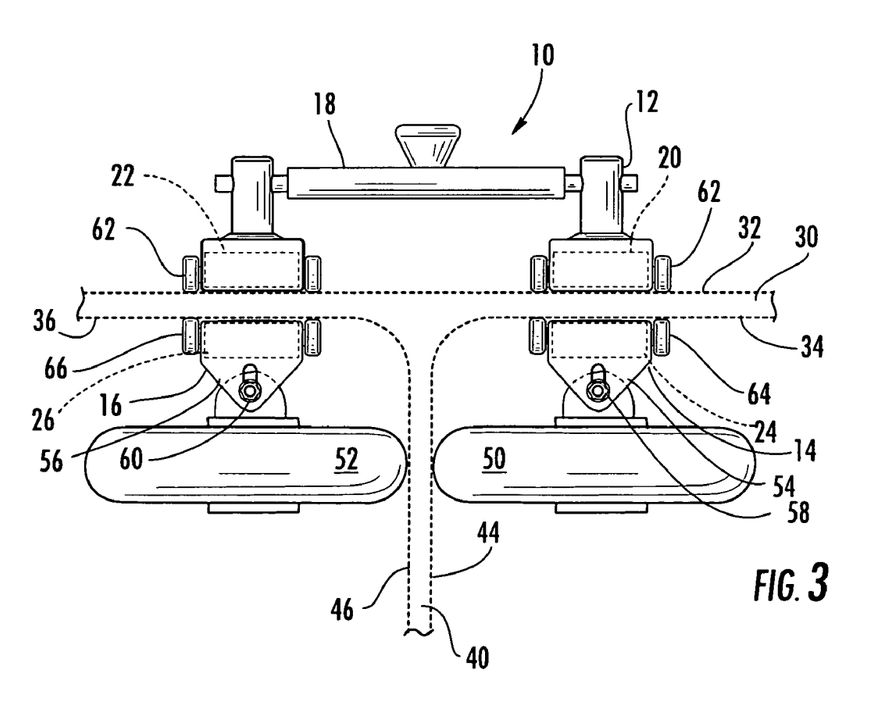
FIG. 3 is a side planar view of the inspection device of FIG. 1, illustrating the inspection device positioned on a structure to inspect limited access features of the structure, wherein the inspection sensors are in a second position relative to the respective housing.

The first inspecting portion 14 and the second inspecting portion 16 of FIGS. 1-3 each include an inspection sensor 50 and 52. The first inspecting portion 14 defines a housing 54 that connects the at least one magnet 24. The inspection sensor 50 of the first inspecting portion 14 is selectively moveable relative to the housing 54 of the first inspecting portion. Similarly, the inspection sensor 52 of the second inspecting portion 16 is selectively moveable relative to the housing 56 of the second inspecting portion. Therefore, the inspection sensors 52 and 54 of the inspection device 10 are configured to inspect multiple positions of the structure 30, such as the feature 40 and the joint 42, as shown in FIGS. 3 and 2, respectively, based upon the selected position of the inspection sensor. Referring to the inspection device 10 of FIGS. 1-3, the inspection sensors 50 and 52 are selectively moveable relative to the housing 54 and 56 by a joint 58 and 60, respectively, to allow the inspection sensor to pivot with respect to the respective housing. The joints 58 and 60 of FIGS. 1-3 comprise a slot in the housing 54 and 56, respectively, a through-hole in a flange connected to the inspection sensor 50 and 52, respectively, and a fastener to connect the housing to the respective flange. The fastener, such as a wingnut and bolt assembly to name one non-limiting example, preferably allows selective adjustment of the relative positions of the housing and flange, thereby selectively moving the inspection sensor relative to the housing. Further embodiments of the present invention provide alternative devices for selectively moving the inspection sensor relative to the housing of the inspecting portion. For example, the embodiment of FIG. 4 comprises ultrasonic wheel transducers as the inspection sensors 150 and 152 that are selectively moveable relative to the housings 154 and 156, respectively, wherein multiple slots, fasteners, and through-holes are included to provide additional positions for the inspection sensors relative to the respective housing. Still further embodiments may substitute the fasteners with spring-loaded ball and detent assemblies, to list one non-limiting example, or other devices to provide discrete, predetermined positions for the inspection sensor to be selectively moved relative to the housing.

Figure 8:
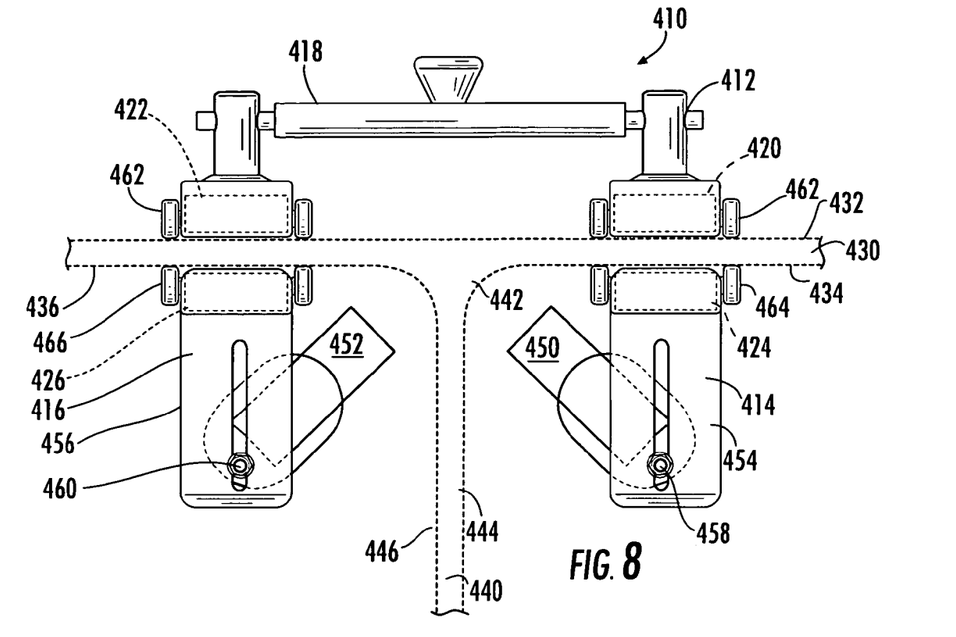
FIG. 8 is a side planar view of a non-destructive inspection device in accordance with a fifth embodiment of the present invention, illustrating an actuating portion and two inspecting portions wherein the inspection sensors are moveable relative to the housing of the respective inspecting portion and the inspection sensors define airborne ultrasonic transducers.
Figure 9:
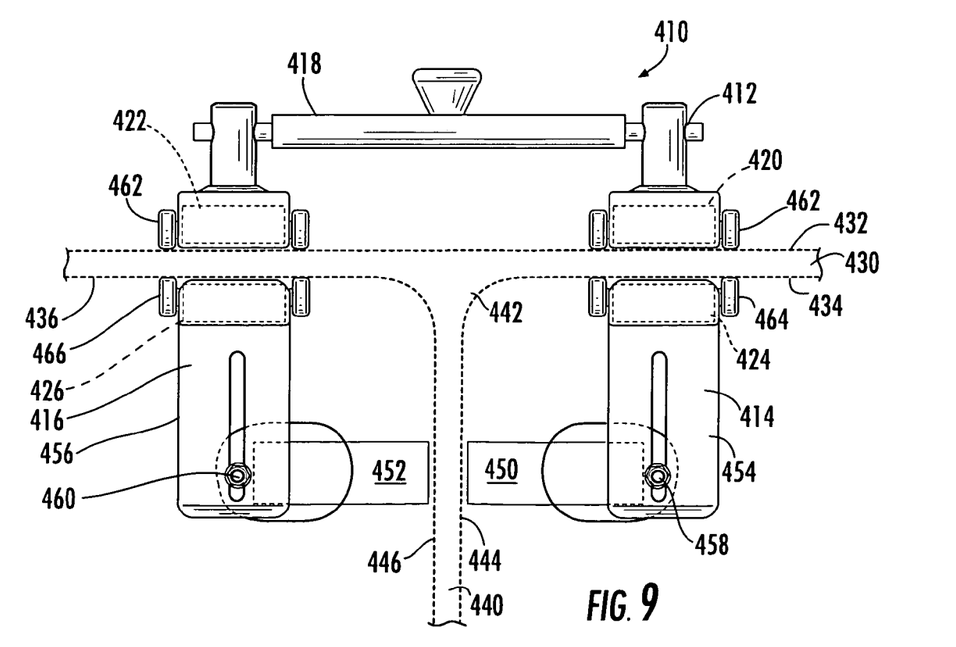
FIG. 9 is a side planar view of the inspection device of FIG. 8, illustrating the inspection sensors in a second position relative to the respective housing.
Figure 10:
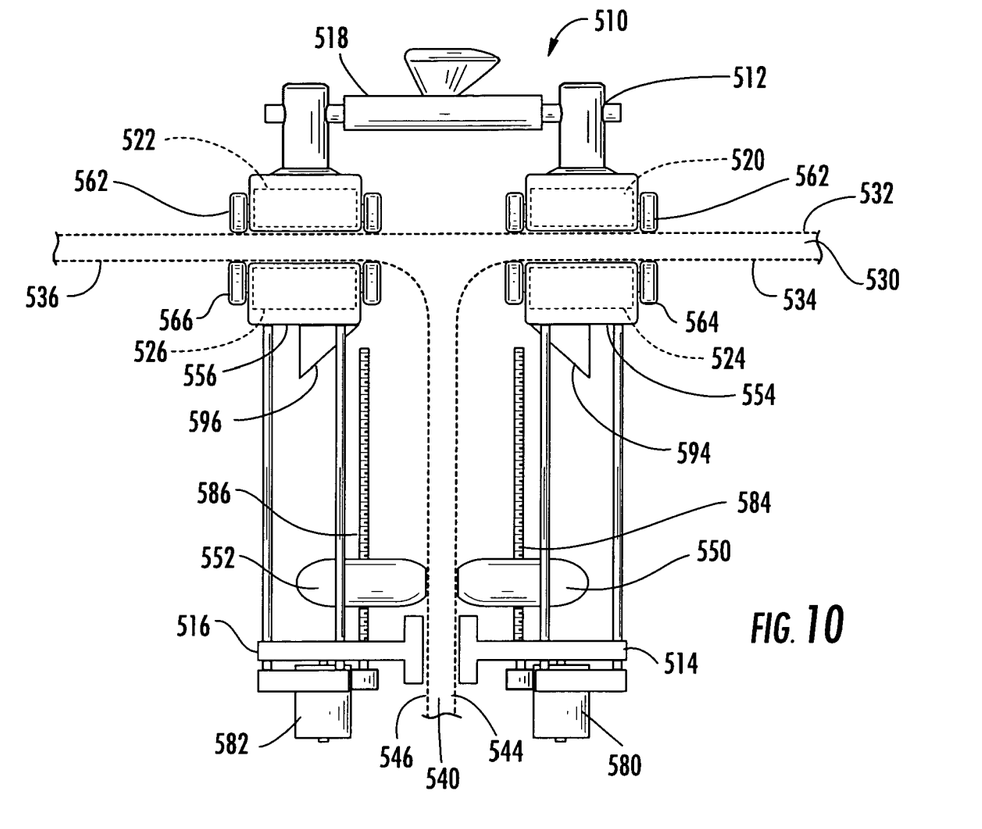
FIG. 10 is a side planar view of a non-destructive inspection device in accordance with a sixth embodiment of the present invention, illustrating an actuating portion and two inspecting portions wherein the inspecting portions include a motor device to selectively move the inspection sensors relative to the housing of the respective inspecting portion.
Figure 11:
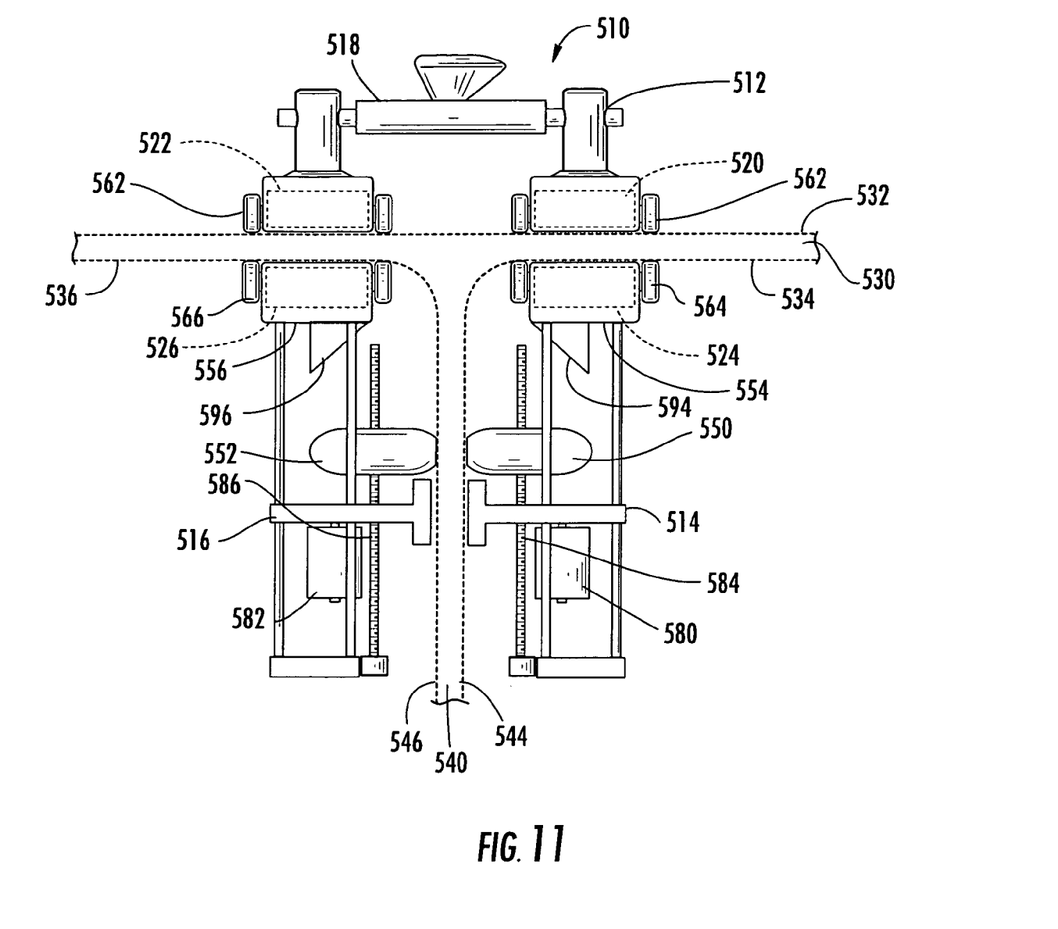
FIG. 11 is a side planar view of the inspection device of FIG. 10, illustrating the inspection sensors in a second position relative to the respective housing.
Figure 12:
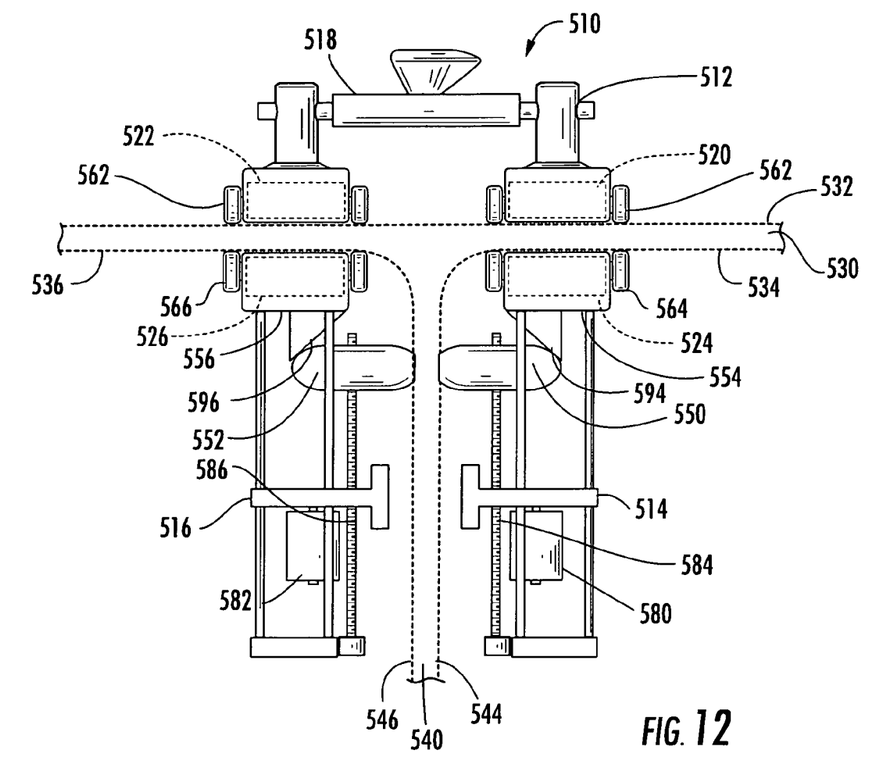
FIG. 12 is a side planar view of the inspection device of FIG. 10, illustrating the inspection sensors in a third position relative to the respective housing.

The inspection sensors 50 and 52 of FIGS. 1-3 comprise a single ultrasonic wheel transducer. Further embodiments of the inspection device may include alternative inspection sensors and any number of inspection sensors. As discussed below with regard to alternative illustrated embodiments, further embodiments of the present invention may include other contact or non-contact inspection sensors such as fiber-optic laser ultrasonic systems, velocimetric or mechanical impedance analysis devices, optical borescopes, miniature cameras, infrared sensors, capacitive sensors, and x-ray sources and detectors, traditional contact pulse-echo and through-transmission ultrasonic transducers, or UT resonance probes, to list a few non-limiting examples. In at least one advantageous embodiment, as illustrated in FIGS. 8 and 9, inspection sensors do not require a couplant; therefore, no clean-up or collection of a couplant is required, which may be very difficult because of the limited access to the feature being inspected.

For a structure 30 comprising a ferromagnetic material in the feature 40, but non-ferromagnetic material in the material through which the actuating portion 12 and inspecting portions 14 and 16 are magnetically coupled, as described above, the inspection sensor(s) may comprise eddy current inspection sensors to inspect the ferromagnetic feature. An example of such a structure is typically a non-aerospace application comprising ferromagnetic spars and non-ferromagnetic skins, as described above.

Figure 4:
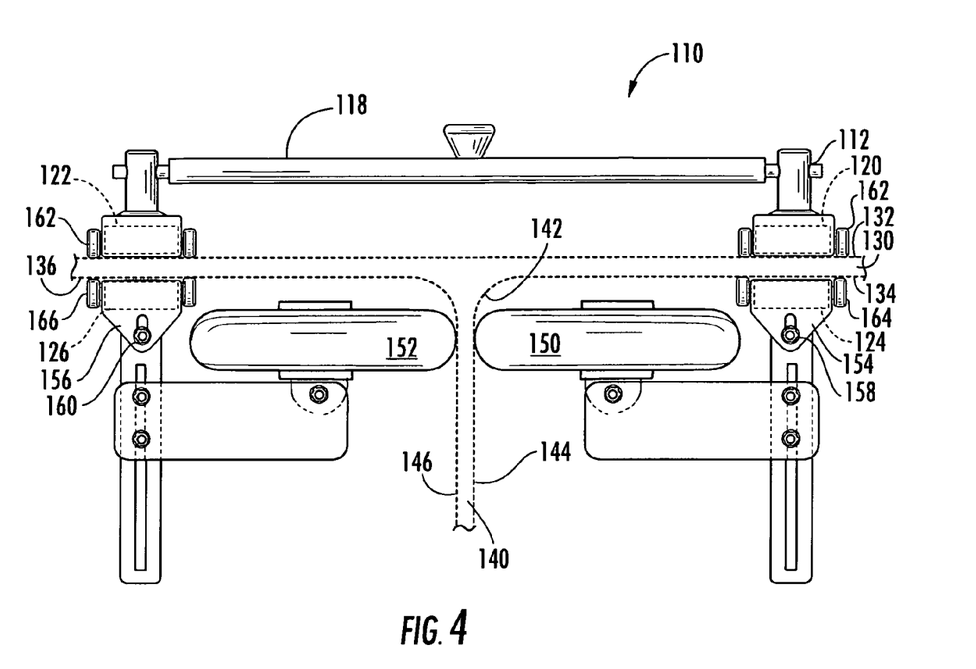
FIG. 4 is a side planar view of a non-destructive inspection device in accordance with a second embodiment of the present invention, illustrating an actuating portion and two inspecting portions wherein the inspection sensors are moveable relative to the housing of the respective inspecting portion.

A set of rollers 62, skids, skis, or the like may be provided on the actuating portion 12 proximate the at least one first magnet 20 and the at least one second magnet 22 to facilitate movement of the actuating portion. In addition, a set of rollers 64, skids, skis, or the like may be provided on the first inspecting portion 14 to facilitate movement along the surface 34. A set of rollers 66, skids, skis, or the like may also be included on the second inspecting portion 16 to facilitate movement along the surface 36. In the illustrated embodiment, the sets of rollers 62, 64, and 66 each include four individual rollers located near the magnet of each portion such that the magnets are nominally suspended above their respective surface, as shown in FIG. 4, so that the magnets do not contact the surface but maintain the magnetic coupling necessary to support and align the inspecting portions 14 and 16 such that the inspecting portions move in concert with the actuating portion 12 during the inspection of the structure. Further embodiments of the inspection device 10 may include sets of rollers, skids, skis, or the like at any location to facilitate movement of the portions of the inspection device or may include surfaces or features to facilitate the movement of the portions.

Operation of the inspection device 10 comprises placing the actuating portion 12 on a first surface 32 of the structure 30 and positioning at least one inspecting portion, such as the first inspecting portion 14, on a surface 34 opposite the first surface such that the inspecting portion is proximate the feature 40 to be inspected. The magnets 20 and 24 magnetically couple the inspecting portion 14 to the actuating portion 12 such that the inspecting portion is supported and aligned. To non-destructively inspect the feature 40, the inspection sensor 50 of the inspecting portion 14 is activated such that the reflected signals received by the inspection sensor 50 are sent, via physical electrical connections or by wireless data transmission to a processing element for analysis and storage and, in one embodiment, for creating an output on a display that can be monitored by the technician. The displayed output, which may be data in any form such as numeric data or graphic data to list two non-limiting examples, advantageously represents the location and size of internal flaws or defects in the feature being inspected.

The actuating portion 12 is moved along the first surface 32 such that the inspecting portion 14 is correspondingly moved along the surface 34. The inspection device 10 of FIG. 1 may be manually moved by the technician who grasps the handle 18 to advance the actuating portion 12. The inspection device 10 is advanced along the length of the feature 40 (into and out of the page as illustrated in FIGS. 2 and 3) to substantially inspect the feature, such that the processed data is preferably collected for a summary of the overall inspection results to illustrate or indicate any flaws or defects in the inspected feature. The inspection sensor 50 of FIGS. 1-3 is subsequently moved, either manually as described above or automatically as described below with regards to the embodiment of FIGS. 10-13, relative to the housing of the respective inspecting portion 14, and the inspection device 10 is advanced along the length of the feature again to substantially inspect the feature. This process may be repeated to provide inspection data for multiple sensor positions as desired. After the feature 40 is sufficiently inspected, the inspection device 10 can be removed by pulling the first inspecting portion 14 from the structure 30 to overcome the magnetic couplings and then removing the actuating portion 12. Notably, the technician can inspect the feature 40 in a relatively blind manner since the technician generally does not need to access the surface 34 of the structure proximate the feature, other than to initially position the first inspecting portion 14 and to retrieve the first inspecting portion following the inspection.

The inspection device 10 may also be operated with two or more inspecting portions. The actuating portion 12 is placed on a first surface 32 of the structure 30, the first inspecting portion 14 is positioned on a surface 34 opposite the first surface, and the second inspecting portion 16 is positioned on a surface 36 that is also opposite the first surface such that the feature 40 to be inspected is located between the inspecting portions. The magnet of each portion magnetically couples the inspecting portions 14 and 16 to the actuating portion 12 such that the inspecting portions are supported by the actuating portion and aligned with the actuating portion. The inspecting portions 14 and 16 are also in generally fixed relative positions with respect to each other when each is magnetically coupled to the actuating portion 12. To non-destructively inspect the feature 40, the inspection sensors 50 and 52 of the inspecting portions 14 and 16, respectively, are activated such that the signals transmitted by the first inspection sensors 50 pass through the feature 40 and are received by the second inspection sensors 52 prior to being sent to a processing element for analysis and storage and, in one embodiment, for creating an output on a display that can be monitored by the technician. The actuating portion 12 is moved along the first surface 32 such that the inspecting portions 14 and 16 are correspondingly moved along the surfaces 34 and 36. The inspection device 10 of FIG. 1 may be manually moved by the technician who grasps the handle 18 to advance the actuating portion 12. The inspection device 10 is advanced along the length of the feature 40 to fully inspect the feature, such that the processed data is preferably collected for a summary of the overall inspection results to illustrate or indicate any flaws or defects in the inspected feature. The inspection sensors 50 and 52 of FIGS. 1-3 are subsequently moved, either manually as described above or automatically as described below with regards to the embodiment of FIGS. 10-13, relative to the housing of the respective inspecting portions 14 and 16, respectively, and the inspection device 10 is advanced along the length of the feature again to substantially inspect the feature. This process may be repeated to provide inspection data for multiple sensor positions as desired. After the feature 40 is sufficiently inspected, the inspection device 10 can be removed by pulling the inspecting portions 14 and 16 from the structure 30 to overcome the magnetic couplings and then removing the actuating portion 12. Similar to the inspection with one inspecting portion, the technician can inspect the feature 40 in a relatively blind manner since the technician generally does not need to access the surfaces 34 and 36 of the structure proximate the feature, other than to initially position the inspecting portions 14 and 16 and to retrieve the inspecting portions following the inspection.

Figure 5:
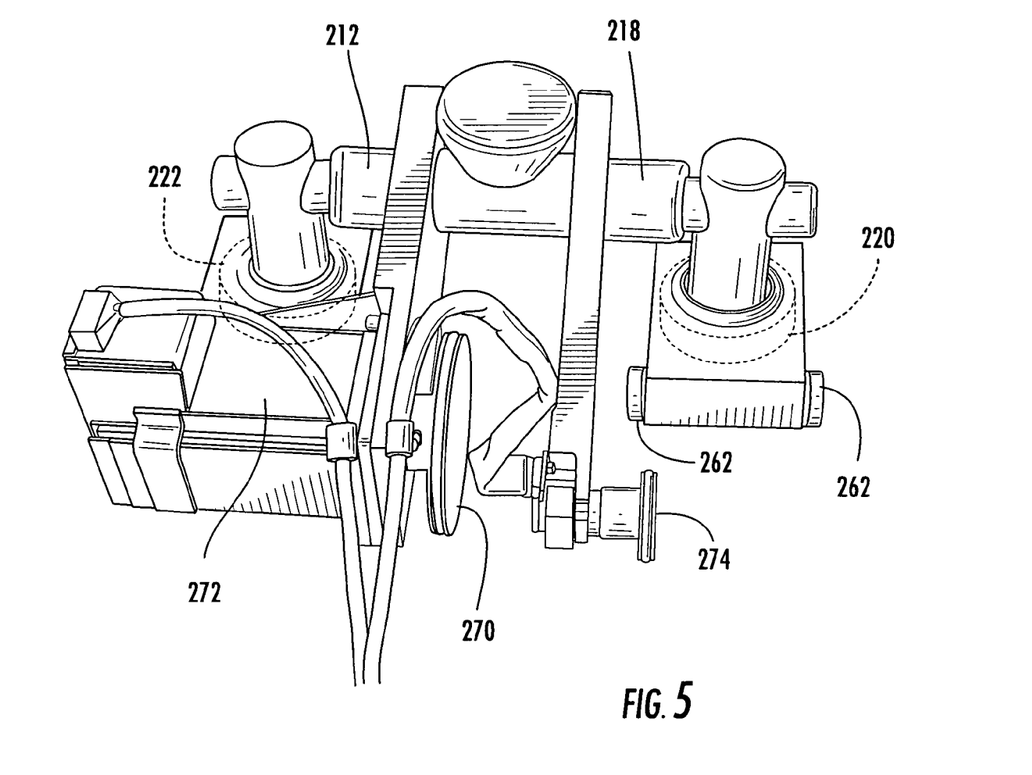
FIG. 5 is a perspective view of an actuating portion of a non-destructive inspection device in accordance with a third embodiment of the present invention, illustrating an actuating portion that includes a motorized drive wheel and a positional encoder device.

FIG. 5 illustrates an actuating portion 212 of a third embodiment of the inspection device of the present invention. The inspecting portions of the second embodiment of the inspection device are not shown to better illustrate the features of the actuating portion 212. The actuating portion 212 includes a motorized drive wheel 270 that is rotated by a motor 272 to provide for motorized positioning of the actuating portion 212 and the corresponding inspecting portions. The motorized drive wheel 270 allows a technician to control the inspection device from a terminal connected to the actuating portion and the inspecting portions so that the inspection device may be remotely controlled to generate data from the inspection sensors that may be processed and displayed, such as by a processing element. Therefore, the inspection device with the actuating portion 212 of FIG. 5 may be moved without manual contact by the technician, as required by the inspection device 10 of FIGS. 1-3. The drive wheel 270 of FIG. 5 contacts the surface of the structure that the actuating portion 212 is placed upon and advantageously includes a textured surface to provide sufficient friction so that the drive wheel does not slip relative to the surface of the structure. A motor power supply (not shown) operated by a technician or with automated equipment provides power to the motor 272 to rotate the drive wheel 270 either forward or backward as required to perform the inspection.

The actuating portion 212 of the inspection device of FIG. 5 also includes a positional encoder device 274. The positional encoder device 274 advantageously provides position data for the inspection device for more accurate or informative inspection results. The positional encoder device 274, which may be mounted to the actuating portion 212, as illustrated in FIG. 5, or to one or more inspecting portions of alternative embodiments (not shown), sends a signal to a processing element indicating the position of the actuating portion 212, or the inspecting portions, which corresponds to the location of the inspection device. The positional encoder device 274 may measure the movement or location of the actuating portion and/or the inspecting portion(s) to which it is attached relative to any surface of the structure or relative to any frame of reference integral to the structure or independent of the structure being inspected. The processing element that advantageously receives the signal from the positional encoder device 274 may correlate the signal from the positional encoder device to the signals received from the inspection sensors so that any detected defects or flaws are accurately located on the structure. The positional encoder device 274 of FIG. 5 is an encoder wheel that produces a signal that corresponds to the rotation of the encoder wheel that contacts the surface that the actuating portion 212 is placed upon, which further corresponds to the location of the inspection device. Further embodiments of the present invention may include a positional encoder device that alternatively measures the movement and/or location of the inspection device, a non-limiting example being an optical encoder that optically measures movement of the inspection device, for more accurate or informative inspection results.

Figure 6:
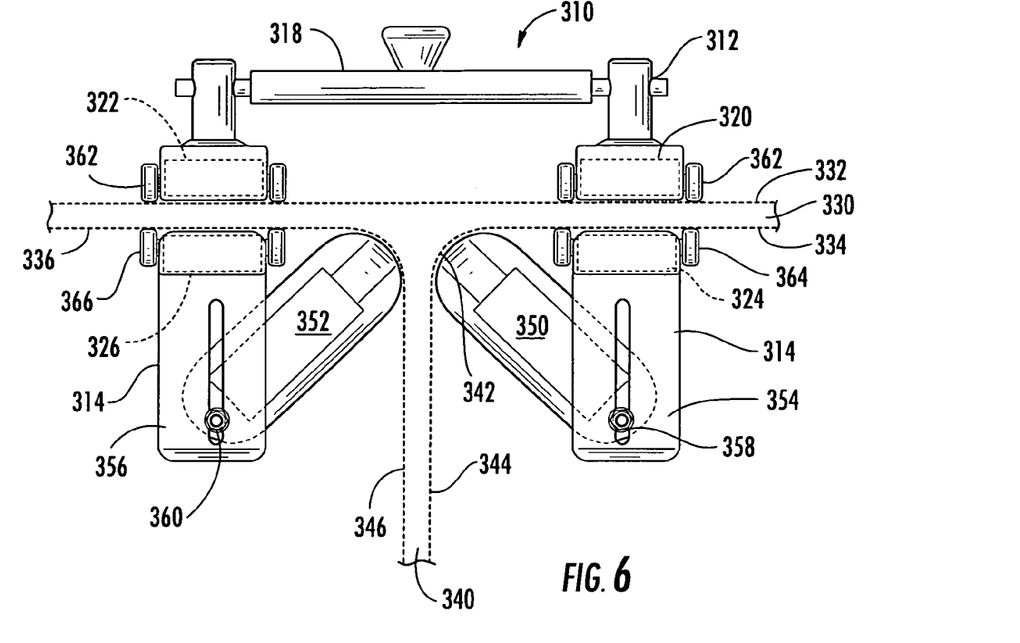
FIG. 6 is a side planar view of a non-destructive inspection device in accordance with a fourth embodiment of the present invention, illustrating an actuating portion and two inspecting portions wherein the inspection sensors are moveable relative to the housing of the respective inspecting portion and the inspection sensors define ultrasonic transducers.
Figure 7:
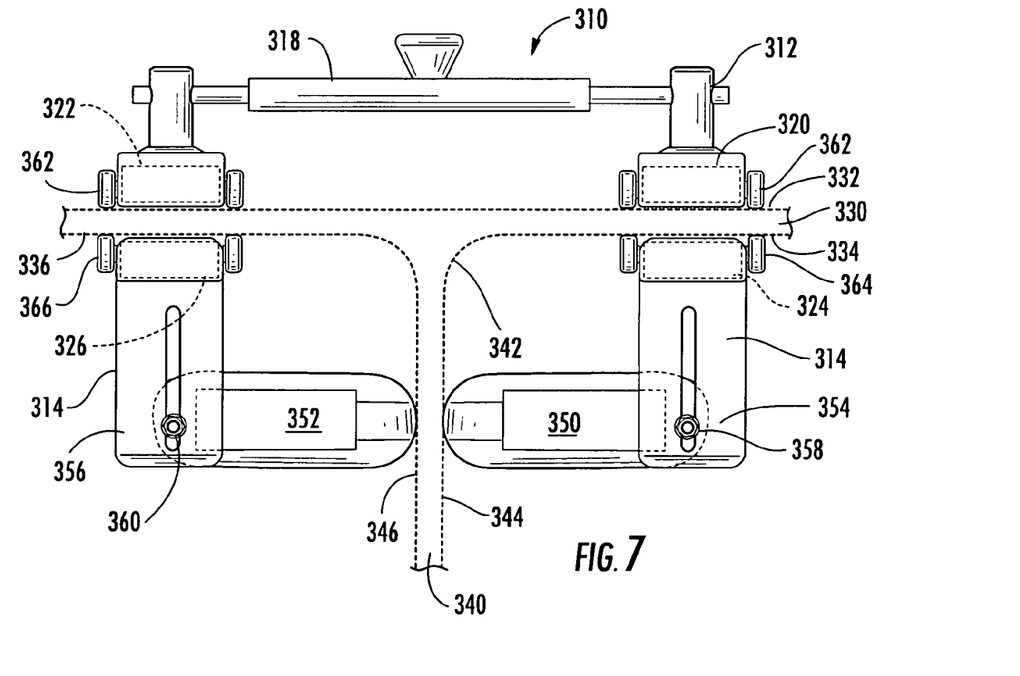
FIG. 7 is a side planar view of the inspection device of FIG. 6, illustrating the inspection sensors in a second position relative to the respective housing.

FIGS. 6 and 7 illustrate a fourth embodiment of the inspection device 310 that includes a first inspecting portion 314 and second inspecting portion 316, wherein the inspection sensors 350 and 352, respectively, comprise ultrasonic shoe transducers, wherein the inspection sensors are selectively moveable relative to the housing 354 and 356, respectively, of the respective inspecting portion. In addition, FIGS. 8 and 9 illustrates a fifth embodiment of the inspection device 410 that includes a first inspecting portion 414 and second inspecting portion 416, wherein the inspection sensors 450 and 452, respectively, comprise airborne ultrasonic transducers, wherein the inspection sensors are selectively moveable relative to the housing 454 and 456, respectively, of the respective inspecting portion. The embodiments of FIGS. 1-4 and 6-9 illustrate inspection sensors that are selectively rotated about an axis that is generally aligned with the direction of motion of the actuating portion and inspecting portion.

Figure 13:
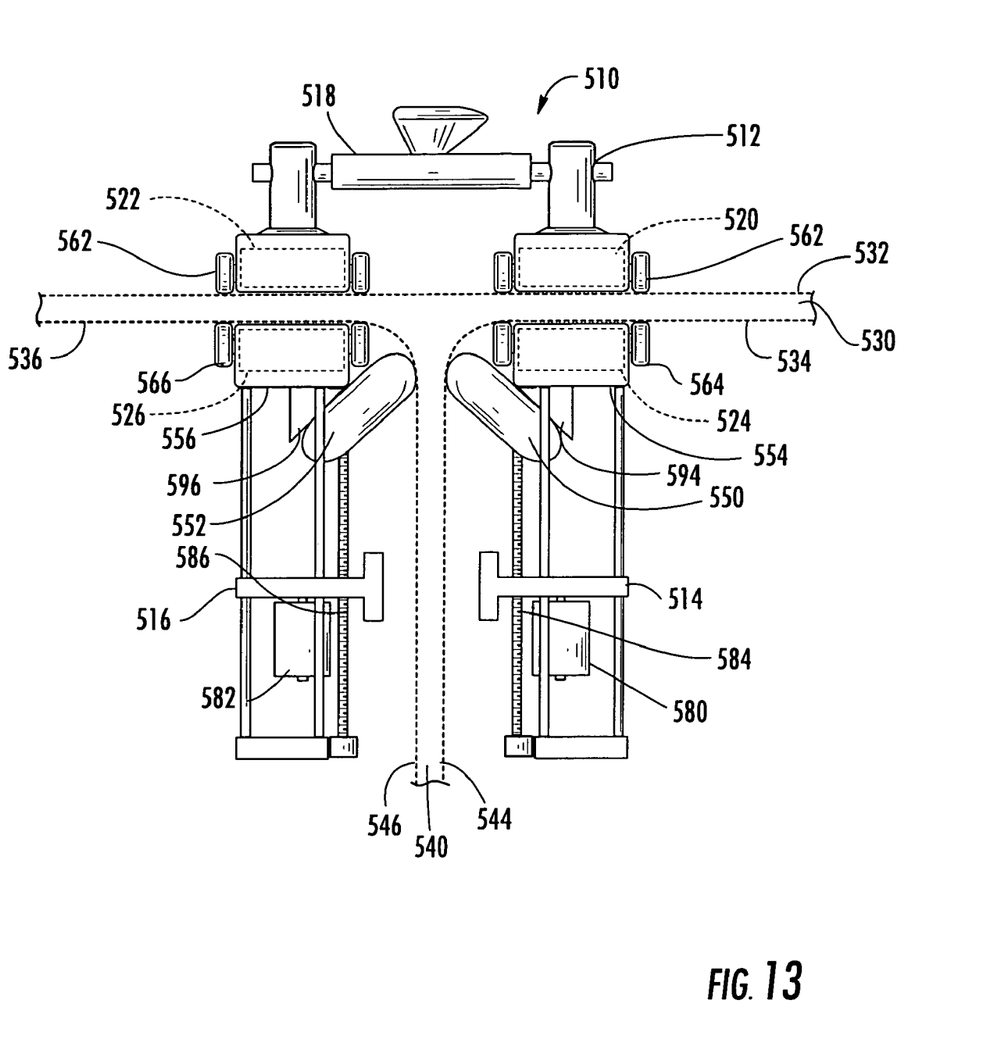
FIG. 13 is a side planar view of the inspection device of FIG. 10, illustrating the inspection sensors in a fourth position relative to the respective housing.

FIGS. 10-13 illustrate a sixth embodiment of the inspection device 510 of the present invention, wherein the inspection sensors 550 and 552 are selectively moveable relative to the housings 554 and 556 of the first and second inspecting portions 514 and 516, respectively, by a motor device 580 and 582. The embodiment of the present invention illustrated in FIGS. 10-13 includes inspection sensors that are selectively movable in a direction that is toward and/or away from the actuating portion and that are selectively rotated about an axis that is generally aligned with the direction of motion of the actuating portion and inspecting portion. The inspection sensors 550 and 552 of FIGS. 10-13 are ultrasonic wheel transducers through which threaded rods 584 and 586, respectively, are positioned, such that rotation of the motor devices 580 and 582, respectively, advances the ultrasonic wheel transducer in a direction substantially aligned with the axis of the threaded rods, which is a direction that is toward and/or away from the actuating portion. Actuating of the motor devices 580 and 582 rotates the threaded rods 584 and 586 such that the inspection sensors 550 and 552, respectively, are advanced toward and/or away from the actuating portion 512. The inspection sensors 550 and 552 are therefore capable of inspecting a substantial portion of the feature 540. In addition, as illustrated in FIG. 13, the inspection sensors 550 and 552 contact tapered surface 594 and 596, respectively, to pivot the inspection sensor about axis that is generally aligned with the direction of motion of the actuating portion 512 and inspecting portion 514 to thereby enable inspection of the joint 542. Still further embodiments of the present invention provide alternative devices for automatically or manually moving the inspection sensor relative to the housing of the inspecting portion. Actuation of the motor devices 580 and 582 of FIGS. 10-13 may be controlled by an operator or may be conducted in a predetermined sequence, and control of the motor devices is provided by physical electrical connects or by wireless communications, or by processing circuitry mounted directly or indirectly to the motor device. Further embodiments of the present invention provide alternative techniques for actuating the motor device.

The inspection device of the present invention provides many improvements to non-destructive inspection techniques. The inspection device permits the inspection of features having limited access that may be difficult for a technician to reach or access. Inspections may also be conducted with or without couplants or may be performed with a single inspection sensor or a plurality of sensors arranged in various configurations. In addition, the inspection device provides for one-sided inspections of features, which is particularly advantageous when the opposite side of the feature is inaccessible. Furthermore, the inspection device provides remote control for convenient operation by the technician and simplified processing and monitoring of the inspection data. The inspection device also allows inspection of a relatively large area by providing inspection sensors that are selectively moveable relative to the housing of the respective inspecting portion. Still further improvements to non-destructive inspection techniques apparent to one skilled in the art are also provided by the inspection device of the present invention.

Many modifications and other embodiments of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A non-destructive inspection device for inspecting a feature of a structure, the inspection device comprising:

an actuating portion having at least one magnet, wherein the actuating portion is structured for placement on a first surface of the structure such that the actuating portion is movable relative to the structure; and an inspecting portion comprising a housing, a moveable inspection sensor and at least one magnet, wherein the inspecting portion is structured for positioning on a second surface of the structure opposite the first surface such that the inspecting portion is magnetically coupled to the actuating portion so that movement of the actuating portion causes the inspecting portion to move in concert with the actuating portion without the inspecting portion directly contacting the actuating portion;

wherein the inspection sensor is at least one of selectively moveable relative to the housing of the inspecting portion in a direction generally toward and/or away from the actuating portion or selectively rotatable about an axis that is generally aligned with the direction of motion of the actuating portion and inspecting portion.

2. A non-destructive inspection device according to claim 1 wherein the moveable inspection sensor of the inspecting portion comprises an ultrasonic transducer.

3. A non-destructive inspection device according to claim 1 wherein the moveable inspection sensor of the inspecting portion comprises an ultrasonic wheel transducer.

4. A non-destructive inspection device according to claim 1 wherein the moveable inspection sensor of the inspecting portion comprises an airborne ultrasonic transducer.

5. A non-destructive inspection device according to claim 1 wherein the inspecting portion includes a plurality of magnets and the actuating portion includes a plurality of magnets magnetically coupled to the plurality of magnets of the inspecting portion.

6. A non-destructive inspection device according to claim 5 wherein the inspecting portion includes a set of rollers proximate the plurality of magnets and the actuating portion includes a set of rollers proximate the plurality of magnets.

7. A non-destructive inspection device according to claim 1 wherein the actuating portion includes a motorized drive wheel for motorized positioning of the actuating portion.

8. A non-destructive inspection device according to claim 7 wherein the actuating portion includes a positional encoder device to monitor the positioning of the actuating portion.

9. A non-destructive inspection device for inspecting a feature of a structure, the inspection device comprising:

an actuating portion having at least one first magnet and at least one second magnet, wherein the actuating portion is structured for placement on a first surface of the structure such that the actuating portion is movable relative to the structure;

a first inspecting portion inspecting portion comprising a housing, a moveable inspection sensor and at least one magnet, wherein the first inspecting portion is structured for positioning on a surface of the structure opposite the first surface such that the first inspecting portion is magnetically coupled to the first magnet of the actuating portion so that movement of the actuating portion causes the first inspecting portion to move in concert with the actuating portion without the first inspecting portion directly contacting the actuating portion; and a second inspecting portion comprising a housing, a moveable inspection sensor and at least one magnet, wherein the second inspecting portion is structured for positioning on a surface of the structure opposite the first surface such that the feature of the structure to be inspected is located between the first inspecting portion and the second inspecting portion, wherein the second inspecting portion is magnetically coupled to the second magnet of the actuating portion so that movement of the actuating portion causes the second inspecting portion to move in concert with the actuating portion without the second inspecting portion directly contacting the actuating portion, and wherein the first inspecting portion and the second inspecting portion are in a generally fixed relative position with respect to each other when each is magnetically coupled to the actuating portion;

wherein the first moveable inspection sensor is selectively moveable relative to the housing of the first inspecting portion and the second moveable inspection sensor is selectively moveable relative to the housing of the second inspecting portion.

10. A non-destructive inspection device according to claim 9 wherein the first moveable inspection sensor of the first inspecting portion comprises an ultrasonic transmitter and the second moveable inspection sensor of the second inspecting portion comprises an ultrasonic receiver.

11. A non-destructive inspection device according to claim 9 wherein the first moveable inspection sensor of the first inspecting portion comprises an ultrasonic wheel transducer and the second moveable inspection sensor of the second inspecting portion comprises an ultrasonic wheel transducer.

12. A non-destructive inspection device according to claim 9 wherein the first moveable inspection sensor of the first inspecting portion comprises an airborne ultrasonic transducer and the second moveable inspection sensor of the second inspecting portion comprises an airborne ultrasonic transducer.

13. A non-destructive inspection device according to claim 9 wherein the actuating portion includes a motorized drive wheel for motorized positioning of the actuating portion.

14. A non-destructive inspection device according to claim 13 wherein the actuating portion includes a positional encoder device to monitor the positioning of the actuating portion.

15. A method of inspecting a feature of a structure, comprising:

placing an actuating portion of a non-destructive inspection device on a first surface of the structure, wherein the actuating portion has at least one magnet;

positioning at least first and second inspecting portions of the non-destructive inspection device on a second surface of the structure opposite the first surface such that the feature of the structure to be inspected is located between the first and second inspecting portions, wherein the first and second inspecting portions each comprise a housing, a moveable inspection sensor, and at least one magnet such that positioning the respective inspecting portion comprises magnetically coupling a magnet of the actuating portion to the magnet of the respective inspecting portion;

moving the actuating portion on the first surface of the structure such that the first and second inspecting portions are moved in concert with the actuating portion;

moving the moveable inspection sensor of at least one inspecting portion relative to the housing of the inspecting portion; and monitoring an output from the moveable inspection sensor of at least one inspecting portion.

16. A method according to claim 15, further comprising moving the second moveable inspection sensor relative to the housing of the second inspecting portion.

17. A non-destructive inspection device according to claim 15 wherein the feature of the structure extends from the second surface of the structure and wherein moving the actuating portion further comprises moving the actuating portion such that the inspecting portion inspects the feature of the structure extending from the second surface of the structure.

18. A method according to claim 15 wherein moving the moveable inspection sensor comprises selectively rotating the moveable inspection sensor about an axis that is generally aligned with the direction of motion of the actuating portion and inspecting portion.

19. A method according to claim 15 wherein moving the moveable inspection sensor comprises selectively moving the moveable inspection sensor in a direction generally toward and/or away from the actuating portion.

20. A non-destructive inspection device for inspecting a feature of a structure, the inspection device comprising:

an actuating portion having at least one magnet, wherein the actuating portion is structured for placement on a first surface of the structure such that the actuating portion is movable relative to the structure;

an inspecting portion comprising a housing, a moveable inspection sensor and at least one magnet, wherein the inspecting portion is structured for positioning on a second surface of the structure opposite the first surface such that the inspecting portion is magnetically coupled to the actuating portion so that movement of the actuating portion causes the inspecting portion to move in concert with the actuating portion without the inspecting portion directly contacting the actuating portion; and a motor device configured to controllably position the inspection sensor relative to the housing of the inspecting portion.

21. A non-destructive inspection device for inspecting a feature of a structure, the inspection device comprising:

an actuating portion having at least one first magnet and at least one second magnet, wherein the actuating portion is structured for placement on a first surface of the structure such that the actuating portion is movable relative to the structure;

a first inspecting portion inspecting portion comprising a housing, an inspection sensor and at least one magnet, wherein the first inspecting portion is structured for positioning on a surface of the structure opposite the first surface such that the first inspecting portion is magnetically coupled to the first magnet of the actuating portion so that movement of the actuating portion causes the first inspecting portion to move in concert with the actuating portion without the first inspecting portion directly contacting the actuating portion; and a second inspecting portion comprising a housing, an inspection sensor and at least one magnet, wherein the second inspecting portion is structured for positioning on a surface of the structure opposite the first surface such that the feature of the structure to be inspected is located between the first inspecting portion and the second inspecting portion, wherein the second inspecting portion is magnetically coupled to the second magnet of the actuating portion so that movement of the actuating portion causes the second inspecting portion to move in concert with the actuating portion without the second inspecting portion directly contacting the actuating portion;

wherein the inspection sensor of at least one of the first or second inspecting portion is selectively moveable relative to the housing of the respective inspecting portion.

* * * * *